United States Patent [19]
Lesher

[11] Patent Number: 4,839,355
[45] Date of Patent: Jun. 13, 1989

[54] TRICYCLIC-PYRIDINYLQUINOLINE COMPOUNDS, THEIR PREPARATION AND USE

[75] Inventor: George Y. Lesher, Schodak, N.Y.

[73] Assignee: Sterling Drug Inc., New York, N.Y.

[21] Appl. No.: 220,717

[22] Filed: Jul. 18, 1988

Related U.S. Application Data

[63] Continuation-in-part of Ser. No. 94,611, Sep. 9, 1987, abandoned.

[51] Int. Cl.$^4$ .................. A61K 31/535; A61K 31/54; C07D 498/06; C07D 513/06
[52] U.S. Cl. ................ 514/224.5; 514/230.2; 544/32; 544/101
[58] Field of Search ............... 544/101, 32; 514/230.2, 514/224.5

[56] References Cited

U.S. PATENT DOCUMENTS

| | | | |
|---|---|---|---|
| 3,753,993 | 8/1973 | Lesher et al. | 260/286 |
| 3,840,544 | 10/1974 | Lorenz et al. | 546/156 |
| 4,382,892 | 5/1983 | Hayakawa et al. | 260/243.3 |
| 4,529,725 | 7/1985 | Chu | 546/156 |
| 4,540,694 | 9/1985 | Chu | 514/232 |
| 4,636,506 | 1/1987 | Gilligan et al. | 514/256 |
| 4,638,067 | 1/1987 | Culbertson et al. | 546/156 X |
| 4,698,350 | 10/1987 | Daum et al. | 546/156 X |

FOREIGN PATENT DOCUMENTS 179239 4/1986 European Pat. Off. .

*Primary Examiner*—Richard L. Raymond
*Attorney, Agent, or Firm*—Thomas L. Johnson; Paul E. Dupont

[57] ABSTRACT

Fluorinated 10-(2,6-dimethyl-4-pyridinyl)-3-methyl-7-oxo-2,3-dihydro-7H-pyrido[1,2,3-de][1,4]benzoxazine-6-carboxylic acids and -benzothiazine-6-carboxylic acids of the formula

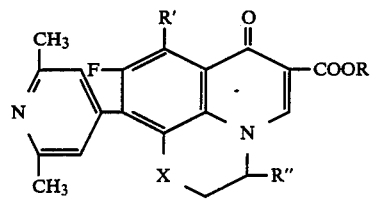

wherein R is hydrogen, R' is hydrogen or fluoro, R" is alkyl of 1-3 carbon atoms and X is O or S are superior antibacterial agents.

10 Claims, No Drawings

TRICYCLIC-PYRIDINYLQUINOLINE COMPOUNDS, THEIR PREPARATION AND USE

This application is a continuation-in-part of copending application Ser. No. 094,611, filed Sept. 9, 1987, now abandoned.

BACKGROUND OF THE INVENTION

1. Field of the Invention

This invention relates to novel substituted 4-oxo-3-quinolinecarboxylic acids, to methods for the preparation thereof, and compositions and methods for the use thereof as anitbacterial agents.

2. Information Disclosure Statement

Antibacterially active 4-oxo-3-quinolinecarboxylic acids are known in the prior art which includes the following references.

Lesher and Carabateas U.S. Pat. No. 3,753,993, issued Aug. 21, 1973, discloses 7-(2,6-dimethyl-4-pyridinyl)-1-ethyl-1,4-dihydro-4-oxo-3-quinolinecarboxylic acid.

Sterling Drug Inc. European Patent Application, published Apr. 30, 1986 under No. 179,239, discloses 7-(2,6-dimethyl-4-pyridinyl)-1-ethyl-6-fluoro-1,4-dihydro-4-oxo-3-quinolinecarboxylic acid.

Hayakawa et al. U.S. Pat. No. 4,382,892, issued May 10, 1983, discloses 9-fluoro-3-methyl-10-(4-methyl-1-piperazinyl)-7-oxo-2,3-dihydro-7H-pyrido[1,2,3-de][1,4]benzoxazine-6-carboxylic acid:

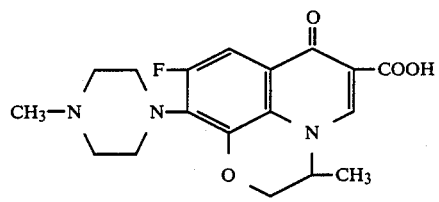

also known under the generic name ofloxacin.

D. T. Chu U.S. Pat. No. 4,540,694, issued Sept. 10, 1985, discloses a genus of 1-pyridine-substituted quinobenzoxazines having the formula

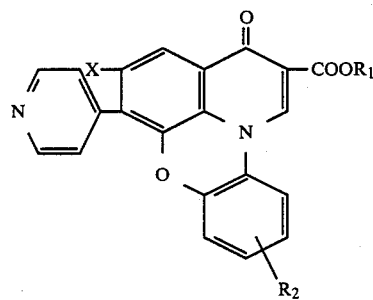

wherein X is halogen or hydrogen; $R_2$ is a substituent; and $R_1$ is hydrogen or a carboxy protecting group. The specification of the patent suggests substitution on the pyridine ring including alkyl groups but there are no specific examples thereof.

Gilligan et al. U.S. Pat. No. 4,636,506, issued Jan. 13, 1987, discloses a genus of compounds of the formula

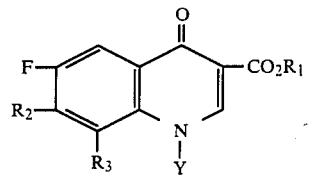

wherein $R_1$ is hydrogen, a pharmaceutically acceptable cation or alkyl of 1 to 3 carbon atoms;

Y is selected from the group consisting of alkyl and haloalkyl of 1 to 3 carbon atoms, alkyl, vinyl, cyclopropyl, hydroxyethyl, phenyl, 4-hydroxyphenyl and 4-fluorophenyl;

$R_2$ is 3-pyridyl or 4-pyridyl which may be substituted by various groups not including alkyl;

$R_3$ is fluoro; or $R_3$ and Y may be combined to form a bridge of the formula $-X(CH_2)_n-CHR_4-$ or $-X-(CH_2)_n-C(=CH_2)-$ wherein X is $CH_2$, O, S, NH or $NCH_3$;

n is 0, 1 or 2, and $R_4$ is selected from the group consisting of hydrogen, alkyl and halo alkyl of 1 to 3 carbon atoms, hydroxymethyl, hydroxyethyl, aminoethyl and phenyl.

The only specific compounds disclosed where $R_3$ and Y are combined are Examples 7 and 8 which respectively have the following structures:

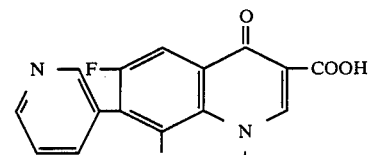

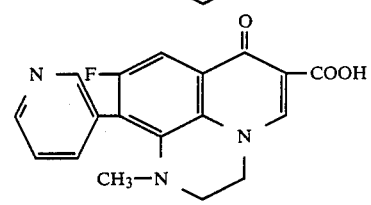

SUMMARY OF THE INVENTION

In a product aspect, the invention relates to compounds of the formula:

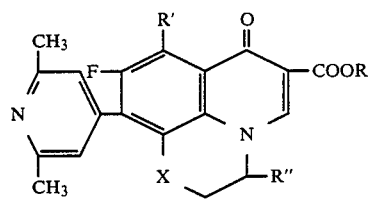

wherein:

R is hydrogen or lower-alkyl;

R' is selected from the group consisting of hydrogen, fluoro and $-SR'''$, where $R'''$ is benzyl, phenyl or lower-alkyl;

R'' is alkyl of 1-3 carbon atoms;

X is O or S; and to pharmaceutically acceptable acid-addition salts thereof; and to alkali metal or amine salts of compounds where R is hydrogen.

Particularly preferred compounds are those where R is hydrogen and R' is hydrogen or fluoro, which compounds possess outstanding antibacterial activity.

In a further product aspect the invention relates to compositions for combating bacteria which comprise an antibacterially effective amount of a compound of Formula I wherein R is hydrogen and R' is hydrogen or fluoro in admixture with a suitable carrier or diluent.

In a process aspect, the invention relates a process for preparing a compound of Formula I where R is H and R' is H or F, and X is O which comprises (a) reacting a compound of the formula

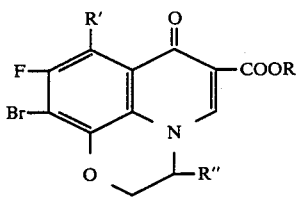

II wherein R is lower-alkyl, with a compound of the formula:

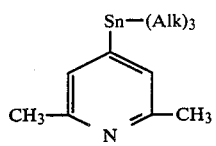

wherein Alk is alkyl of 1–6 carbon atoms, in the presence of a palladium complex catalyst; and (b) hydrolyzing the resulting ester to produce the corresponding carboxylic acid where R is hydrogen.

In a further process aspect, the invention relates to a process for preparing a compound of Formula I where R and R' are both hydrogen which comprises:

(a) reacting a compound of Formula I, where R' is fluoro, with a sulfide, R'''SH, in the presence of sodium hydride to produce a compound of Formula I where R' is —SR'''; and (b) heating the compound with Raney nickel to replace the —SR''' group by hydrogen.

In a still further process aspect, the invention relates to a process for preparing a compound according to Formula I where R' is H or F and X is S which comprises (a) reacting a compound of the formula:

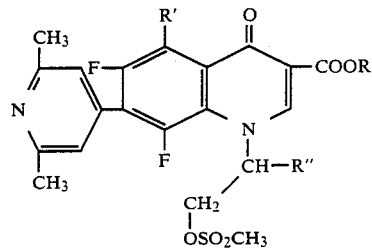

wherein R is lower-alkyl, with hydrogen sulfide in the presence of sodium hydride; and (b) hydrolyzing the resulting ester to produce the corresponding carboxylic acid where R is hydrogen.

In a still further process aspect, the invention relates to a method of combating bacteria which comprises contacting the locus of said bacteria, including administration to a mammalian host, with a composition containing an antibacterially effective amount of a compound of Formula I where R is hydrogen and R' is hydrogen or fluror.

DETAILED DESCRIPTION INCLUSIVE OF PREFERRED EMBODIMENTS

In the definitions of R and R' in Formula I above, the term "lower-alkyl" stands for alkyl preferably having one to six carbon atoms which may be straight or branched.

The invention also contemplates pharmaceutically acceptable acid-addition salts of the compounds of Formula I. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like.

The compounds of Formula I where R' is hydrogen can also be prepared and used in the form of their alkali metal or amine salts, preferably the sodium, potassium, ethylenediamine or N-methylglucamine salts.

The compounds of Formula I are prepared according to the following flow sheets:

FLOW SHEET A

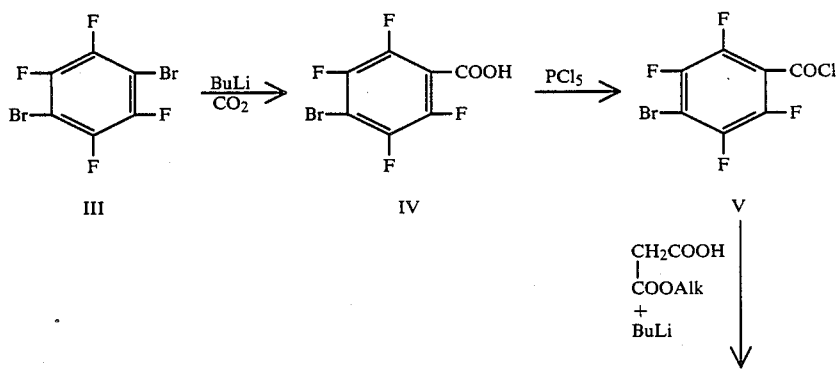

-continued
FLOW SHEET A

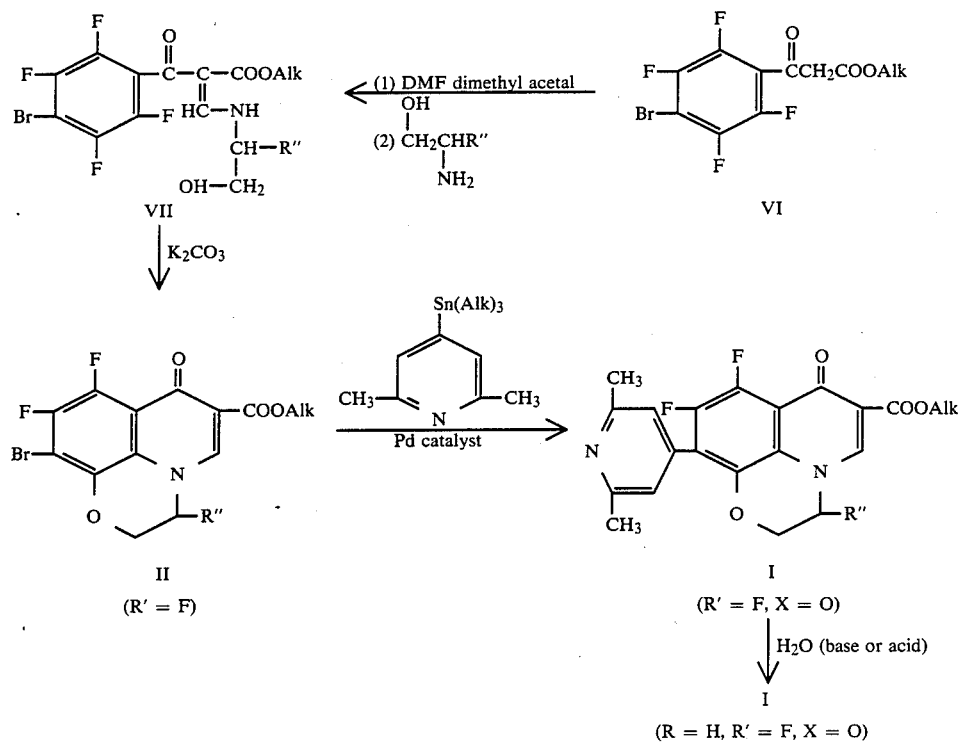

The above Flow Sheet A illustrates the preparation of 10-(2,6-dimethyl-4-pyridinyl)-8,9-difluoro-3-methyl-7-oxo-2,3-dihydro-7H-pyrido[1,2,3-de][1,4]benzoxazine6-carboxylic acid. 1,4-Dibromo-2,3,5,6-tetrafluorobenzene (III) is metalated with butyllithium and then caused to react with carbon dioxide to give 4-bromo-2,3,5,6-tetrafluorobenzoic acid (IV). The latter is converted to its acid chloride (V) which reacts with a half ester of malonic acid in the presence of butyllithium to afford an alkyl 4-bromo-2,3,5,6-tetrafluorobenzoylacetate (VI). The benzoylacetate (VI) is then treated with molar equivalent amounts of dimethylformamide (DMF) dimethyl acetal and 2-amino-1-alkanol to produce an alkyl N-(1-hydroxy-2-alkyl)-3-amino-2-(4-bromo-2,3,5,6-tetrafluorobenzoyl)propenoate (VII). The latter is then cyclized by heating with a base, preferably potassium carbonate, to give a compound of Formula II (R'=F). The alkyl 10-bromo-8,9-difluoro-3-alkyl-7-oxo-2,3-dihydro-7H-pyrido[1,2,3-de][1,4]benzoxazine-6-carboxylate (II) is then caused to react with a 2,6-dimethyl-4-(trialkylstannyl)pyridine in the presence of a palladium complex catalyst thereby producing a compound of Formula I where R'=F and X=O. The latter can then be converted to the free acid (I; R=H, R'=F, X=O) by a conventional hydrolysis reaction with base or acid.

In the conversion of II to I, the process is carried out using approximately equimolar amounts of II and the organotin compound in an inert solvent at a temperature between about 50° C. and 100° C., conveniently at the reflux temperature of the solvent. The reaction is complete in a period ranging from 1–24 hours. Alternatively, the reactants and catalyst can be heated in a pressurized vessel in an inert atmosphere (e.g. argon or nitrogen) at a temperature between about 125° and 175° C. until the reaction is complete (1–5 hours). The palladium complex catalyst, present to the extent of about 5 mole percent, can be any such catalyst known to effect cross-coupling of organotin compounds with organic halides [cf. Kosugi et al., Bull. Chem. Soc. Japan 59, 677–679 (1986)], for example, PdCl$_2$(PPh$_3$)$_2$, Pd(PPh$_3$)$_4$, PdCl$_2$[P(o-tolyl)$_3$]$_2$, PdCl$_2$+2P(OEt)$_3$ and PdCl$_2$(PhCN)$_2$. A preferred catalyst is dichlorobis(triphenylphosphine)palladium [PdCl$_2$-(PPh$_3$)$_2$].

In the compounds of Formula I, the 3-position bearing an alkyl group is an asymmetric center; therefore, the compounds may be obtained as racemic foams or as optically active enantiomeric (R and S) forms depending upon the stereochemical nature of the 2-amino-1-alkanol used in the conversion of VI to VII (Flow Sheet A).

FLOW SHEET B

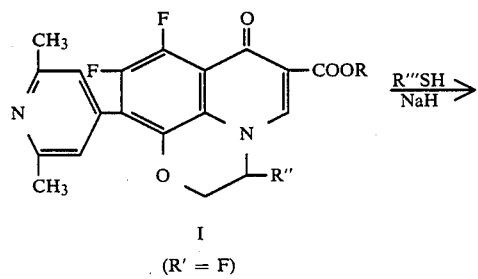

-continued
FLOW SHEET B

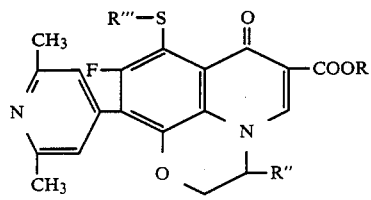

I
(R' = SR''')

↓ Raney Ni

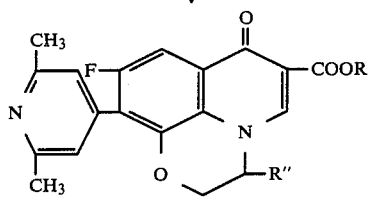

I
(R' = H)

The above flow sheet illustrates the preparation of 10-(2,6-dimethyl-4-pyridinyl)-9-fluoro-3-alkyl-7-oxo-2,3-dihydro-7H-pyrido[1,2,3-de][1,4]benzoxazine-6-carboxylic acid (I; R and R'=H, X=O). The starting material is a compound of Formula I where R'=F prepared according to Flow Sheet A. The reaction can be carried out either on the ester (R=alkyl) or the free acid (R=H). The difluoro compound is caused to react with a thiol (R'''SH) in the presence of sodium hydride to give the corresponding compound where the 8-fluoro substituent is replaced by R'''—S—. When the latter compound is heated with Raney nickel in a solvent such as ethanol, the thiol group is removed to give I (R'=H, X=O).

The compounds of Formula I where R'=H and X=O can alternatively be prepared by a process which avoids the removal of the 8-fluoro substituent (Flow Sheet B). The alternative procedure involves the use of commerically availabe 2,3,4,5-tetrafluorobenzoic acid as a starting material according to the following Flow Sheet C.

FLOW SHEET C

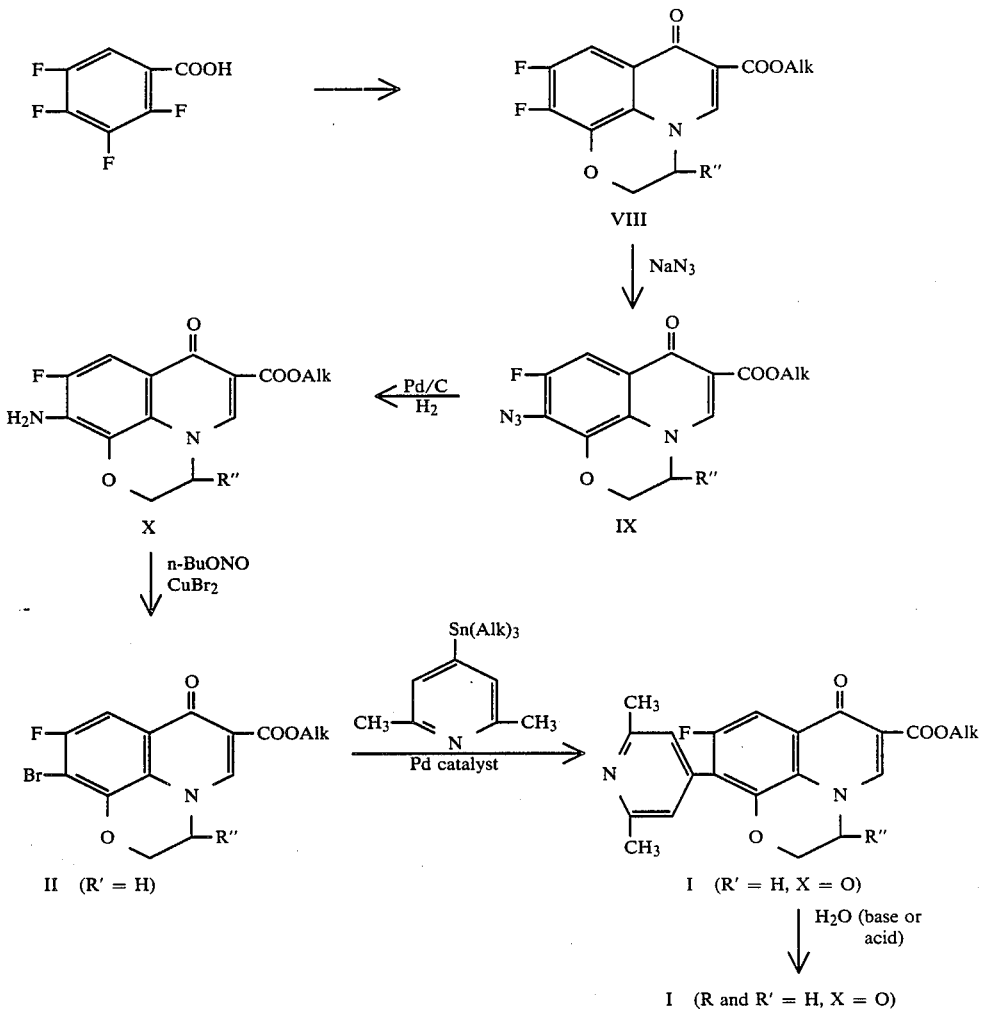

2,3,4,5-Tetrafluorobenzoic acid is converted by a series of reactions analogous to those to Flow Sheet A to alkyl 9,10-difluoro-3-alkyl-7-oxo-2,3-dihydro-7H-pyrido[1,2,3-de][1,4]benzoxazine-6-carboxylate (VIII). The replacement of the 10-fluro substituent by bromine, required for the tin-coupling reaction, is effected by conversion to VIII to the 10-azido compound (IX), reduction to the 10-amino compound (X) and reaction of the latter with n-butyl nitrite and cupric bromide to produce the 10-bromo compound (II; R=H). The coupling reaction with 2,6-dimethyl-4-(trialkylstannyl)pyridine then gives the ester of I (R'=H, X=O) which is hydrolyzed to the free acid I (R and R'=H, X=O).

Compounds of Formula I where X=S are prepared as illustrated by the following Flow Sheet D, starting from the commercially availabe 2,3,4,5-tetrafluorobenzoic acid.

FLOW SHEET D

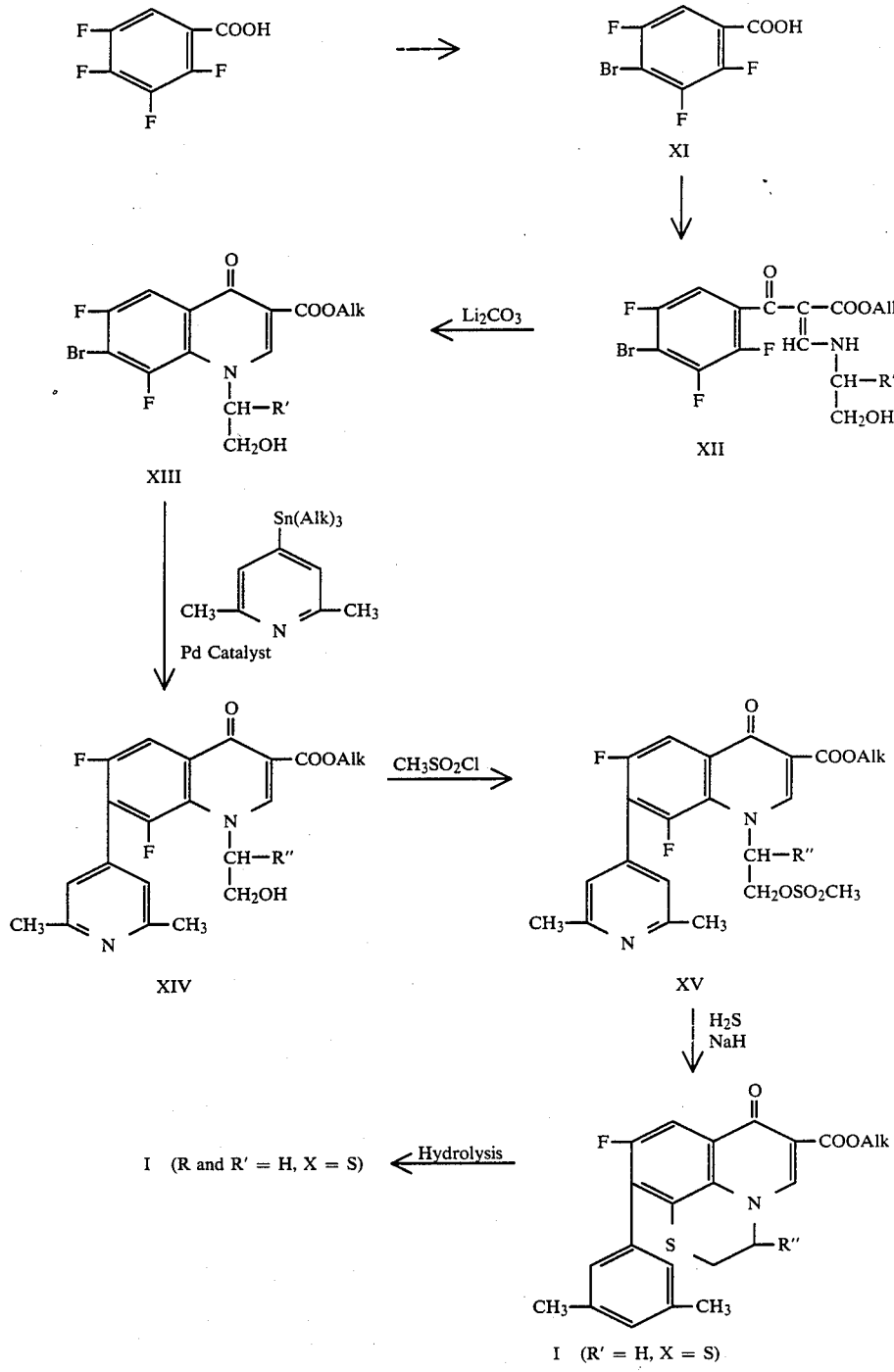

The 4-fluoro substituent of 2,3,4,5-tetrafluorobenzoic acid was replaced by bromine by a series of reactions analogous to the sequence VIII→IX→X→II in Flow Sheet C, to produce 4-bromo-2,3,5-trifluorobenzoic acid (XI). The latter is then converted to a series of reactions analogous to the sequence IV→V→VI→VII of Flow Sheet A to yield an alkyl N-(1-hydroxy-2-alkyl)-3-amino-2-(4-bromo-2,3,5-trifluorobenzoyl)-propenoate (XII). Selective cyclization of XII with lithium carbonate affords an alkyl 7-bromo-6,8-difluoro-1,4-dihydro-1-(2-hydroxy-2-alkyl)quinoline-3-carboxylate (XIII). Coupling with 2,6-dimethyl-4-(trialkylstannyl)pyridine then yields alkyl 6,8-difluoro-7-(2,6-dimethyl-4-pyridinyl)-1,4-dihydro-1-(2-hydroxy-2-alkyl)quinoline-3-carboxylate (XIV). The latter is then converted to its mesylate (XV) with methanesulfonyl chloride. The mesylate is cyclized with hydrogen sulfide and sodium hydride to form the ester I (R'=H, X=S) which by hydrolysis is converted to the free acid (I; R and R'=H, X=S). The cyclization takes place by saturating a solution or suspension of XV with hydrogen sulfide, then treating it with excess sodium hydride while cooling the reaction in a Dry Ice bath and then allowing the reaction to warm to ambient temperature.

The compound of Formula I where R=H, R'=F and X=S can be prepared starting with compound III of Flow Sheet A and proceeding as in Flow Sheet D.

The structures of the compounds were established by the modes of synthesis, by elementary analyses and by infrared, nuclear magnetic resonance, and/or mass spectra.

The following examples will further illustrate the invention.

EXAMPLE 1

(a) 4-Bromo-2,3,5,6-tetrafluorobenzoic acid [IV]

n-Butyllithium (42 ml, 2.4M in hexane) was slowly added to a solution of 30.78 g 1,4-dibromo-2,3,5,6-tetrafluorobenzene in 200 ml tetrahydrofuran cooled to −70° C. under nitrogen. Solid carbon dioxide (about 12 g) was then added to the stirred mixture which was then allowed gradually to warm to 0° C. at which point 16 ml 6M hydrochloric acid and 16 ml water were added. The reaction mixture was concentrated and the residue extracted with methylene dichloride. The extract was washed with concentrated sodium chloride solution, dried (magnesium sulfate) and concentrated to dryness to give 22.23 g (81.5%) 4-bromo-2,3,5,6-tetrafluorobenzoic acid, m.p. 128°–135° C.

(b) 4-Bromo-2,3,5,6-tetrafluorobenzoyl chloride [V]

A mixture of 21.83 g 4-bromo-2,3,5,6-tetrafluorobenzoic acid and 16.7 g phosphorus pentachloride was stirred at room temperature for about three days. The reaction mixture was then distilled under aspirator vacuum to give 20.44 g (88%) of the acid chloride.

(c) Ethyl 4-bromo-2,3,5,6-tetrafluorobenzoylacetate [VI; Alk=C$_2$H$_5$]

n-Butyllithium (192 ml, 2.4M in hexane) was slowly added to a stirred solution of 30.24 g monoethylmalonate and 15 mg 2,2'-bipyridine in 500 ml tetrahydrofuran cooled to −60° to −70° C. under nitrogen. After about half of the butyllithium had been added, the temperature of the mixture was raised to −20° to −25° C. at which temperature the remainder of the butyllithium was added. The reaction mixture was then recooled to −60° to −70° C. and 33.41 g 4-bromo-2,3,5,6-tetrafluorobenzoyl chloride in 10 ml tetrahydrofuran was added. The reaction mixture was allowed to warm to room temperature, stirred overnight, and then poured into 460 ml 1M hydrochloric acid. The organic layer was separated, dried (magnesium sulfate) and concentrated. The residue was dissolved in ether, washed with aqueous potassium bicarbonate solution, dried (magnesium sulfate), concentrated and distilled to give 34.18 g ethyl 4-bromo-2,3,5,6-tetrafluorobenzoylacetate, b.p. 112°–117° C.(0.8 mm.).

(d) Ethyl (S)-2-(4-bromo-2,3,5,6-tetrafluorobenzoyl)-N-(1-hydroxy-2-propyl)-3-aminopropenoate [VII; Alk=C$_2$H$_5$, R''=CH$_3$]

A mixture of 19.99 g ethyl 4-bromo-2,3,5,6-tetrafluorobenzoylacetate and 7.8 ml DMF dimethyl acetal in 60 ml tetrahydrofuran was stirred at room temperature for about 16 hours. The mixture was then cooled in an ice-bath and 4.6 ml (S)-2-amino-1-propanol was added. The resulting clear solution was concentrated in vacuo, and the residue was dissolved in ether and chromatographed on a column of silica gel using ether as eluant. There was obtained 22.4 g of ethyl (S)-2-(4-bromo-2,3,5,6-tetrafluorobenzoyl)-N-(1-hydroxy-2-propyl)-3-aminopropenoate as a light yellow solid, m.p. 127°–134° C., $[\alpha]_D^{25}$=+17.6°.

(e) Ethyl (S)-10-bromo-8,9-difluoro-3-methyl-7l-oxo-2,3-dihydro-7H-pyrido[1,2,3-de][1,4]benzoxazine-6-carboxylate [II; R=C$_2$H$_5$, R'=H, R''=CH$_3$]

A mixture of 22.4 g ethyl 2-(4-bromo-2,3,5,6-tetrafluorobenzoyl)-N-(1-hydroxy-2-propyl)-3-aminopropenoate and 44.3 g potassium carbonate in dimethylformamide was heated to the boiling point, and then allowed to cool to room temperature. The reaction mixture was poured into water, extracted with chloroform, dried (magnesium sulfate) and concentrated in vacuo. The residue was crystallized from ethanol to give 14.47 g ethyl (S)-10-bromo-8,9-difluoro-3-methyl-7-oxo-2,3-dihydro-7H-pyrido[1,2,3-de][1,4benzoxazine-6-carboxylate as a cream-colored solid, m.p. 247°–249.5° C., $[\alpha]_D^{25}$=−74.5° (1% in chloroform).

(f) 2,6-Dimethyl-4-(trimethylstannyl)pyridine

To a mixture of 100 g sodium (30% dispersion in toluene) and 400 ml dimethoxyethane (DME) cooled in an ice-salt bath and under nitrogen was added a solution of 121 g trimethyltin chloride in 50 ml DME over a 2 hour period while keeping the temperature below 5° C. The mixture was stirred at 0°–5° C. for 2.5 hours and then 70 g 4-chloro-2,6-dimethylpyridine in 50 ml DME was added over a 1.5 hour period while keeping the temperature at 0°–10° C. The reaction mixture was stirred at the latter temperature for 1 hour and then allowed to stand at room temperature overnight. The mixture was filtered and concentrated, and the residue treated with ether and again filtered and concentrated. The resulting orange liquid was distilled, collecting the material boiling at 130° C. (20 mm.) to give 80 g 2,6-dimethyl-4-(trimethylstannyl)pyridine.

(g) Ethyl (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylate [I; R=C$_2$H$_5$, R'=F, R''=CH$_3$, X=O]

To a mixture of 14.08 g ethyl (S)-10-bromo-8,9-difluoro-3-methyl-7-oxo-2,3-dihydro-7H-pyrido[1,2,3-de][1,4]benzoxazine-6-carboxylate, 10.91 g 2,6-dimethyl-4-trimethylstannylpyridine and 6.3 ml hexamethylphosphoramide in 200 ml dioxane under nitrogen was added 1.27 g dichlorobis(triphenylphosphine)palladium. The reaction mixture was heated at reflux for 24 hrs. Most of the solvent was then removed in vacuo and the residue was extracted with ethyl acetate and water, and then with chloroform. The organic extracts were combined and concentrated. The residue was chromatographed on silica gel using as eluant chloroform and chloroform containing increasing amounts of methanol (1–3%). There was thereby obtained 2.5 g pure ethyl (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylate, light yellow solid, m.p. 295°–297° C., $[\alpha]_D^{25} = -34.4°$ (1% in chloroform).

(h)
(S)-10-(2,6-Dimethyl-4-pyridinyl)-8,9-difluoro-3-methyl-7-oxo-2,3-dihydro-7H-pyrido[1,2,3-de][1,4]benzoxazine-6-carboxylic acid [I; R=H, R'=F, R"=CH$_3$]

A solution of 1.20 g ethyl (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylate in 15 ml 1M hydrochloric acid was heated at reflux for 2 hours. The reaction mixture was cooled, poured into sodium acetate solution and extracted with methylene dichloride. The extract was dried (sodium sulfate) and concentrated, and the residue was crystallized from methanol to give 0.58 g (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylic acid as a colorless solid, m.p. 307°–310° C., $[\alpha]_D^{25} = -39.1°$ (1% in chloroform).

It is contemplated that by replacing the (S)-2-amino-1-propanol in step (d) above by racemic 2-amino-1-propanol or (R)-2-amino-1-propanol and carrying out the reactions described in the succeeding steps (e)-(h) there can be obtained, respectively, racemic 10-(2,6-dimethyl-4-pyridinyl)-8,9-difluoro-3-methyl-7-oxo-2,3-dihydro-7H-pyrido[1,2,3-de][1,4]benzoxazine-6-carboxylic acid or (R)-10-(2,6-dimethyl-4-pyridinyl)-8,9-difluoro-3-methyl-7-oxo-2,3-dihydro-7H-pyrido[1,2,3-de][1,4]benzoxazine-6-carboxylic acid.

EXAMPLE 2

(a) Ethyl (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylate [I; R=C$_2$H$_5$, R'=F, R"=CH$_3$, X=O]

A mixture of 19.35 g ethyl (S)-10-bromo-8,9-difluoro-3-methyl-7-oxo-2,3-dihydro-7H-pyrido[1,2,3-de][1,4-]benzoxazine-6-carboxylate, 16.20 g 2,6-dimethyl-4-(trimethylstannyl)pyridine, 0.88 g dichlorobis(triphenylphosphine)palladium in 200 ml ethanol was placed in a stainless steel Parr apparatus and the system flushed with nitrogen and pressurized to about 80 psi with nitrogen. The system was heated at 150° C. for 4 hours. The reaction mixture was cooled and concentrated in vacuo, and the residue was taken up in chloroform, filtered and chromatographed on silica gel using 5% methanol in chloroform to give 14.90 g ethyl (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylate.

(b) The product of part (a) (7.84) was hydrolyzed with hydrochloric acid according to the procedure of Example 1(h), and the product was recrystallized from methanol to give 4.98 g (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylic acid [I; R=H, R'=F, R"=CH$_3$, X=O], identical with the product of Example 1(h).

EXAMPLE 3

(a) Ethyl (S)-8-(benzylthio)-10-(2,6-dimethyl-4-pyridinyl)-9-fluoro-3-methyl-7-oxo-2,3-dihydro-7H-pyrido[1,2,3-de][1,4]benzoxazine-6-carboxylate [I; R=C$_2$H$_5$, R'=C$_6$H$_5$CH$_2$S, R"=CH$_3$, X=O]

To a suspension of 2.78 g ethyl (S)-10-(2,6-dimethyl-4-pyridinyl)-8,9-difluoro-3-methyl-7-oxo-2,3-dihydro-7H-pyrido[1,2,3-de][1,4]benzoxazine-6-carboxylate in 67 ml tetrahydrofuran cooled in an ice-bath was added 0.79 ml benzyl mercaptan, followed by 0.34 g sodium hydride (60% in oil, washed with hexane before use) portionwise, and the mixture was stirred for one hour. An additional 0.079 ml benzyl mercaptan was added and stirring continued at room temperature for 3 hours. The reaction mixture was diluted with saturated sodium acetate solution and extracted with ethyl acetate. The extract was washed with water, dried (sodium sulfate) and concentrated. The residue was crystallized from isopropyl acetate to give 1.98 g ethyl (S)-8-(benzylthio)-10-(2,6-dimethyl-4-pyridinyl)-9-fluoro-3-methyl-7-oxo-2,3-dihydro-7H-pyrido[1,2,3-de][1,4]benzoxazine-6-carboxylate, yellow solid, m.p. 175°–178° C.

(b) Ethyl (S)-10-(2,6-dimethyl-4-pyridinyl)-9-fluoro-3-methyl-7-oxo-2,3-dihydro-7H-pyrido[1,2,3-de][1,4]benzoxazine-6-carboxylate [I; R=C$_2$H$_5$, R'=H, R"=CH$_3$, X=O]

A mixture of 1.98 g ethyl (S)-8-(benzylthio)-10-(2,6-dimethyl-4-pyridinyl)-9-fluoro-3-methyl-7-oxo-2,3-dihydro-7H-pyrido[1,2,3-de][1,4]benzoxazine-6-carboxylate and 15 g Raney nickel in 75 ml absolute ethanol was heated at reflux for 10 min. The reaction mixture was cooled, filtered and concentrated in vacuo to give 1.14 g solid product, m.p. 268°–271.5° C. The latter was recrystallized from ethyl acetate and dried at 50° C.(0.1 mm.) to give 0.52 g ethyl (S)-10-(2,6-dimethyl-4-pyridinyl)-9-fluoro-3-methyl-7-oxo-2,3-dihydro-7H-pyrido[1,2,3-de][1,4]benzoxazine-6-carboxylate, m.p. 273°–276° C.

(c) (S)-10-(2,6-Dimethyl-4-pyridinyl)-9-fluoro-3-methyl-7-oxo-2,3-dihydro-7H-pyrido[1,2,3-de][1,4]benzoxazine-6-carboxylic acid [I; R and R'=H, R"=CH$_3$, X=O]

A mixture of 0.52 g ethyl (S)-10-(2,6-dimethyl-4-pyridinyl)-9-fluoro-3-methyl-7-oxo-2,3-dihydro-7H-pyrido[1,2,3-de][1,4]benzoxazine-6-carboxylate and 10 ml 1M hydrochloric acid was heated at reflux for one hour. The reaction mixture was cooled, poured into sodium acetate solution and extracted with chloroform. The extract was dried (sodium sulfate) and concentrated, and the residue was recrystallized from methanol to give 300 mg (S)-10-(2,6-dimethyl-4-pyridinyl)-9-fluoro-3-methyl-7-oxo-2,3-dihydro-7H-pyrido[1,2,3-de][1,4]benzoxazine-6-carboxylic acid, colorless powder, m.p. 305°–308° C., $[\alpha]_D^{25} = -39.8°$.

A suspension of a sample of the foregoing acid in water was treated with a molar equivalent of sodium hydroxide and the resulting solution freeze-dried to obtain the sodium salt of said acid in the form of a hemihydrate, pale yellow powder, m.p. 308°–311° C.(decompn.).

EXAMPLE 4

(S)-8-(Benzylthio)-10-(2,6-dimethyl-4-pyridinyl)-9-fluoro-3-methyl-7-oxo-2,3-dihydro-7H-pyrido[1,2,3-de][1,4]-benzoxazine-6-carboxylic acid

[I; R=H, R'=C$_6$H$_5$CH$_2$S, R''=CH$_3$] was prepared by hydrolysis of 160 mg ethyl ester of Example 3, part (a) with hydrochloric acid, and was obtained (100 mg) in the form of a pale yellow solid, m.p. 237.5°–238.5° C. (from acetonitrile), [α]$_D^{25}$=−5.0°.

It is further contemplated that (S)-8-(benzylthio)-10-(2,6-dimethyl-4-pyridinyl)-9-fluoro-3-methyl-7-oxo-2,3-dihydro-7H-pyrido[1,2,3-de][1,4]benzoxazine-6-carboxylic acid can be treated with Raney nickel in ethanol to give (S)-10-(2,6-dimethyl-4-pyridinyl)-9-fluoro-3-methyl-7-oxo-2,3-dihydro-7H-pyrido[1,2,3-de][1,4]benzoxazine-6-carboxylic acid, the compound of Example 3(c).

EXAMPLE 5

(a) 2,3,4,5-Tetrafluorobenzoyl chloride

Thionyl chloride (2.9 L), 2.5 kg 2,3,4,5-tetrafluorobenzoic acid and 14.5 ml dimethylformamide were charged to a 12 L reaction vessel and warmed at 90°–95° C. for about 90 minutes. The excess thionyl chloride was first removed at atmospheric pressure, then in vacuo. The residue was distilled on a steam bath at water pump pressure collecting the fraction with b.p. 65°–70° C. at about 15 mm resulting in 2635 g (96.2%) of pale yellow distillate.

(b) Ethyl 2,3,4,5-tetrafluorobenzoylacetate

In a nitrogen atmosphere a 50 gallon kettle was charged with 50.9 kg of tetrahydrofuran, 5.2 kg of monoethyl malonate and about 5 g of 2,2'-dipyridyl. After cooling the mixture to −36° C., 41.6 kg of n-butyllithium (15% in hexane) was added over 3 hours maintaining the temperature at −25° to −35° C. The resultant slurry was cooled further to −60° C. and then treated over about 50 minutes with the acid chloride of part (a) at −62° to −54° C. The green/yellow mixture was stirred for 2 hours at ambient temperature and allowed to warm further overnight. The mixture (−24° C.) was quenched (vacuum) into ambient dilute hydrochloric acid (15 L of muriatic acid and 61 L of deionized water). The quench mixture was separated and the organic phase was washed with 2×40 L of deionized water. The combined aqueous phases were back extracted with 40 L of hexane-ether (1:1). All organic layers were combined and washed with 100 L of saturated sodium bicarbonate solution; again back extracting the aqueous phase with 40 L of hexane-ether (1:1). The combined organic layers were concentrated to an oil in vacuo followed by dissolution in 20 L of hexane and repeated concentration to dryness. The hot oil was finally dissolved in 19 L of hexane. The solution was cooled to −5° C. and the crystallized solids were filtered using 4.8 L of cold (−6° C.) hexane as wash. The material was dried in vacuo at room temperature affording 4234 g of product suitable for use in the next step. A second crop was obtained by concentrating the combined filtrate and wash and cooling to low temperature. The combined yield for the first and second crops was 4841 g (74.9%).

(c) Ethyl (S)-9,10-difluoro-2,3-dihydro-3-methyl-7-oxo-7H-pyrido[1,2,3-de][1,4]benzoxazine-6-carboxylate [VIII; R''=CH$_3$]

A 12 L stirred flask with charged with 3.6 L of tetrahydrofuran and 1584 g of ethyl 2,3,4,5-tetrafluorobenzoylacetate (endothermic: solution temperature 5° C.) and 751 g of dimethylformamide dimethyl acetal. Stirring under nitrogen atmosphere for 24 hours at ambient temperature gave a high temperature of 27.5° C. within 4.5 hours. The solution was cooled to 4° C. and maintained at 4°–5° C. while adding a solution of 451 g of (S)-(+)-2-amino-1-propanol and 225 ml of tetrahydrofuran (required 40 minutes using a −5° C. cooling bath). The solution was stirred for 1 hour at 5°–10° C. and then concentrated in vacuo at a pot temperature of 5°–15° C. to a viscous yellow oil. The oil was diluted with 5.4 of dimethylformamide and stirred vigorously while adding 207 g of anhydrous potassium carbonate. The reaction flask was arranged for distillation and heated to 140°–145° C. for 1 hour. The mixture was cooled to room temperature and poured into 54 L of cold water with agitation. Filtration, washing with 6 L of cold water and drying in vacuo at 50° C. gave 1512 g of yellow-buff product. The crude product (2783 g) was passed through a mill to break up lumps before slurrying in refluxing ethanol (5.6 L) for 1 hour. The suspension was cooled to 20° C. and the solid collected and washed with cold ethanol (2.8 L). After drying in vacuo a total of 1556 g (55.9% recovery) was ready for use in the next step.

(d) Ethyl (S)-10-azido-9-fluoro-2,3-dihydro-3-methyl-7-oxo-7H-pyrido[1,2,3-de][1,4]benzoxazine-6-carboxylate [IX; R''=CH$_3$]

Dimethylformamide (3.9 L) and sodium azide (188.3 g) were warmed at 90°–95° C. in a 5 L flask for 5 hours and the resulting slurry was allowed to cool slightly before quenching the mixture into 31 L of deionized water at room temperature. The thin slurry was stirred briefly before collecting the tan crystals using an additional 6 L of room temperature deionized water to wash the filter cake. The solids were dried in vacuo at 40°–45° C. resulting in 701 g of material used directly in the next step.

(e) Ethyl (S)-10-amino-9-fluoro-2,3-dihydro-3-methyl-7-oxo-7H-pyrido[1,2,3-de][1,4]benzoxazine-6-carboxylate [X; R''=CH$_3$]

A slurry of 701 g of ethyl (S)-10-azido-9-fluoro-2,3-dihydro-3-methyl-7-oxo-7H-pyrido[1,2,3-de][1,4]benzoxazine-6-carboxylate in 6.0 of dimethylformamide was charged to the five gallon autoclave. After placing the vessel under nitrogen, a slurry of 45 g of 10% palladium-on-carbon in 700 ml of dimethylformamide was added. The mixture was hydrogenated at 48–50 psi and 600 RPM. A 10° C. rise in temperature was observed during the first thirty minutes of reaction. The reaction mixture was filtered and washed with 2×3 L of dimethylformamide. Concentration of the filtrate under aspirator pressure gave a very thick, dark residue (volume ~700 ml). Ethanol (1.2 L) was added and the suspension was refluxed briefly. After cooling to 0° C., the product was collected, washed with 3×300 ml of cold ethanol and dried for eighteen hours at 80° C. in vacuo to give 508 g of product which was shown to be 97.6% pure by HPLC.

(f) Ethyl (S)-10-bromo-9-fluoro-2,3-dihydro-3-methyl-7-oxo-7H-pyrido[1,2,3-de][1,4]benzoxazine-6-carboxylate [II; R'=H, R''=CH₃]

A 12 L flask equipped with a strong stirrer was charged with 4.3 L of acetonitrile, 433 g of copper (II) bromide and 508 g of ethyl (S)-10-amino-9-fluoro-2,3-dihydro-3-methyl-7-oxo-7H-pyrido[1,2,3-de][1,4]benzoxazine-6-carboxylate. After establishing a nitrogen atmosphere and heating the mixture to 70° C., the heat was turned off. n-Butyl nitrite (290 ml) was added at a rate to reach and maintain reflux (required 20 minutes). Heat was then applied to maintain reflux for 2¾ hours. Using aspirator vacuum the pressure was reduced slightly to distill 2.4 L of acetonitrile while maintaining a pot temperature of 70° C. The concentrate was cooled to 50° C. and poured slowly into a stirred mixture of 12 L of cold water and 2.1 L of 12N hydrochloric acid. After 1 hour the acidic slurry was filtered and washed with 4 L of water. The filter cake was then washed with dilute ammonium hydroxide (1 part ammonium hydroxide to 3 parts water). A final wash with 2 L of water and drying in vacuo at 60° C. gave 406 g of light tan crude product. The crude product was added to 2.1 L of methanol and refluxed for 3 hours. Cooling to 5° C., washing with 0.2 L of cold methanol and drying in vacuo at 50° C. gave 318 g of product.

(g) 2,6-Dimethyl-4-(tributylstannyl)pyridine

A 22 L flask was charged with 740 g of 4-bromo-2,6-lutidine and 10.0 L of diethyl ether and cooled to −60° C. in a Dry Ice/acetone bath under nitrogen. A solution of 4.0 moles of n-butyllithium was added dropwise over 1 hour maintaining a temperature below −58° C. to form an orange-yellow precipitate. After continued stirring in the cold for 15 minutes, 1280 g of tributyltin chloride was added over 2 hours at a temperature of −60° to −57° C. to form a solution. The reaction was stirred cold for 45 minutes before it was slowly (2 hours) warmed to 20° C. A portion of Super-Cel (100 g) was added and the reaction mixture was filtered to remove the precipitated lithium chloride. The cake was washed with diethyl ether (2×500 mL). After concentration to dryness a total of 1575 g (99.7% yield) of product was obtained which was used without further purification.

(h) Ethyl (S)-10-(2,6-dimethyl-4-pyridinyl)-9-fluoro-2,3-dihydro-3-methyl-7-oxo-7H-pyrido[1,2,3-de][1,4]benzoxazine-6-carboxylate [I; R'=H, R''=CH₃, X=O]

A 5 L flask was charged with 355 g of the bromoester of part (f), 423 g of 2,6-dimethyl-4-(tributylstannyl)pyridine, 20.4 g of dichlorobis(triphenylphosphine)palladium and 243 ml of dimethylformamide and heated slowly to 140° C. The heater was removed allowing the reaction to reach an exotherm at 165° C. After the exotherm had subsided, the reaction was heated to above 140° C. for 2 hours. The cooled mixture was dissolved in 4 L of a 50% mixture of chloroform-water and filtered to remove the spent catalyst. The filter cake was washed with chloroform. The organic layer was separated and dried over magnesium sulfate. The drying agent was filtered and washed with 500 ml of chloroform. The combined filtrate and wash was concentrated to produce a crystalline solid which was slurried for 1 hour in 1.8 L of diethyl ether. The solid was collected and washed with 4×250 ml of diethyl ether followed by air drying under a hood. A total of 327 g (85.9% yield) of the product was used in the next step without further purification.

(i) (S)-10-(2,6-Dimethyl-4-pyridinyl)-9-fluoro-3-methyl-7-oxo-7H-pyrido[1,2,3-de][1,4]benzoxazine-6-carboxylic acid [I; R and R'=H, R''=CH₃, X=O]

A 22 L flask was charged with 698 g of the ester of part (h), 10 L of deionized water and 915 ml of concentrated hydrochloric acid and heated to above 90° C. for 2 hours to form a greenish-gray solution. Activated charcoal (Darco G-60) (35 g) was added and the mixture was filtered hot. The cake was washed with 2.0 L of hot deionized water. The cooled solution was first washed with 3.0 L of ethyl acetate and then basified with 2.0 L of 35% sodium hydroxide forming a solid over 2 hours. The sodium salt of the product was dissolved by heating the system to 80° C. and the product was precipitated with the addition of 200 ml of glacial acetic acid to pH (5.5). After stirring at 80° to 85° C. for one hour the solid was collected while hot and washed with 4×1.0 L of deionized water. The product was purified as follows. A 5 L flask was charged with 2.5 L of dimethylformamide and 730 g of crude product and the mixture was heated to 140° C. to form a clear dark solution. After cooling to 5° C. the precipitate which formed at 110° C. was collected and washed with 2.5 L of deionized water. The solids were dried in vacuo at 60° C. for 64 hours affording 493 g of I (R and R''=H, X=O), identical with the product of Example 3(c).

EXAMPLE 6

(a) 4-Bromo-2,3,5-trifluorobenzoic acid [XI]

158°–159° C., was prepared from the commercially available 2,3,4,5-tetrafluorobenzoic acid by a method analogous to the procedures of steps (d), (e) and (f) of Example 5, i.e. reaction with sodium azide to form 4-azido-2,3,5-trifluorobenzoic acid, reduction of the latter to 4-amino-2,3,5-trifluorobenzoic acid, m.p. 215°–218° C., and replacement of the amino group by bromine using t-butyl nitrite and cupric bromide.

(b) Ethyl 4-bromo-2,3,5-trifluorobenzoylacetate m.p. 51°–59° C. was prepared by reaction of 4-bromo-2,3,5-trifluorobenzonic acid with phosphorus pentachloride as in Example 1(b) to form the acid chloride, and reaction of the latter with n-butyllithium and monoethyl malonate according to the procedure of Example 1(c).

(c) Ethyl (R)-2-(4-bromo-2,3,5-trifluorobenzoyl)-N-(1-hydroxy-2-propyl)-3-aminopropenoate was prepared from ethyl 4-bromo-2,3,5-trifluorobenzoylacetate, dimethylformamide and (R)-2-amino-1-propanol by the procedure of Example 1(d) and obtained in 91% yield as an orange oil.

(d) Ethyl (R)-10-bromo-9-fluoro-2-methyl-7-oxo-2,3-dihydro-7H-pyrido[1,2,3-de][1,4]benzoxazine-6-carboxylate

[II; R=C₂H₅, R'=H, R''=CH₃] was prepared by cyclization of the compound of part (c) above with potassium carbonate according to the procedure of Example 1(c). The crude product was used directly in the next reaction.

(e) Ethyl (R)-10-(2,6-dimethyl-4-pyridinyl)-9-fluoro-3-methyl-7-oxo-2,3-dihydro-7H-pyrido[1,2,3-de][1,4]benzoxazine-6-carboxylate

[I; R=C$_2$H$_5$, R'=H, R''=CH$_3$] was prepared from the 10-bromo compound of part (d) and 2,6-dimethyl-4-tributylstannylpyridine in the presence of dichlorobis(triphenylphosphine)palladium catalyst according to the procedure of Example 2, and was obtained in about 80% yield as a solid, m.p. 267°–273° C.

(f) (R)-10-(2,4-Dimethyl-4-pyridinyl)-9-fluoro-3-methyl-7-oxo-2,3-dihydro-7H-pyrido[1,2,3-de][1,4]benzoxazine-6-carboxylic acid

[I; R and R'=H, R''=CH$_3$] was prepared by hydrolysis of the ester of part (e) with hydrochloric acid according to the procedure of Example 1(h), and was obtained as a colorless solid, m.p. 308°–312° C. when recrystallized from methanol; $[\alpha]_D^{25} = +40.7°$ (1% in chloroform).

EXAMPLE 7

(a) Ethyl (S)-2-(4-bromo-2,3,5-trifluorobenzoyl)-N-(1-hydroxy-2-propyl)-3-aminopropenoate

[XII; Alk=C$_2$H$_5$, R''=CH$_3$] was prepared from ethyl 4-bromo-2,3,5-trifluorobenzoylacetate (Example 6b), dimethylformamide and (S)-2-amino-1-propanol by the procedure of Example 1(d), and was obtained in 74% yield as a solid, m.p. 104°–108° C.

(b) Ethyl (S)-7-bromo-6,8-difluoro-1-(1-hydroxy-2-propyl)-1,4-dihydro-4-oxo-3-quinolinecarboxylate [XIII; Alk=C$_2$H$_5$, R''=CH$_3$]

A mixture of 6.30 g ethyl (S)-2-(4-bromo-2,3,5-trifluorobenzoyl)-N-(1-hydroxy-2-propyl)-3-aminopropenoate and 1.13 g lithium carbonate was heated at 85° C. for 18 hours. The reaction mixture was poured into water and extracted with ethyl acetate. The extracts were dried over magnesium sulfate and concentrated. The residue was recrystallized from acetonitrile to give 3.87 g (65%) of XIII, m.p. 187°–189° C.; $[\alpha]_D = -140.9°$ (chloroform).

(c) Ethyl (S)-7-(2,6-dimethyl-4-pyridinyl)-6,8-difluoro-1-(1-hydroxy-2-propyl)-1,4-dihydro-4-oxo-3-quionlinecarboxylate

[XIV; Alk=C$_2$H$_5$, R''=CH$_3$] was obtained from 3.77 g ethyl (S)-7-bromo-6,8-difluoro-1-(1-hydroxy-2-propyl)-1,4-dihydro-4-oxo-3-quinolinecarboxylate, 3.19 g 2,6-dimethyl-4-(trimethylstannyl)pyridine and 250 mg dichlorobis(triphenylphosphine)palladium in 300 ml ethanol according to the procedure of Example 2, affording 2.33 g of product, colorless solid, m.p. 191°–193° C.

(d) Ethyl (S)-7-(2,6-dimethyl-4-pyridinyl)-6,8-difluoro-1-[1-(methylsulfonyloxy)-2-propyl]-1,4-dihydro-4-oxo-3-quinolinecarboxylate [XV; Alk=C$_2$H$_5$, R''=CH$_3$]

A solution of 1.98 g ethyl (S)-7-(2,6-dimethyl-4-pyridinyl)-6,8-difluoro-1-(1-hydroxy-2-propyl)-1,4-dihydro-4-oxo-4-quinolinecarboxylate and 1.33 ml triethylamine in 25 ml methylene dichloride was cooled to −70° C. and 0.55 ml methanesulfonyl chloride was added. The mixture was stirred and slowly allowed to warm to ambient temperature, then washed with water and aqueous sodium acetate, dried over sodium sulfate and concentrated to give 2.31 g of solid product, m.p. 180°–183° C.

(e) Ethyl (S)-10-(2,6-dimethyl-4-pyridinyl)-9-fluoro-3-methyl-7-oxo-2,3-dihydro-7H-pyrido[1,2,3-de][1,4]benzothiazine-6-carboxylate [I; R=C$_2$H$_5$, R'=H, R''=CH$_3$, X=S]

A mixture of 2.00 g ethyl (S)-7-(2,6-dimethyl-4-pyridinyl)-6,8-difluoro-1-[1-(methylsulfonyloxy)-2-propyl]-1,4-dihydro-4-oxo-3-quinolinecarboxylate and 40 ml tetrahydrofuran was saturated with hydrogen sulfide gas. The mixture was cooled in a Dry Ice/isopropyl alcohol bath and 390 mg sodium hydride (from 60% mixture in oil; oil removed by washing with hexane) was added. The cooling bath was removed and the reaction mixture allowed to stand for three hours. The mixture was poured into ice-water, made neutral with hydrochloric acid and sodium acetate solution, and extracted with chloroform. The chloroform extract was washed with sodium acetate solution and sodium chloride solution, dried (sodium sulfate), filtered and concentrated in vacuo to give 1.84 g of solid product, m.p. 237°–239° C. when recrystallized from acetonitrile.

(f) (S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid [I; R and R'=H, R''=CH$_3$, X=S]

A mixture of 0.95 g ethyl (S)-10-(2,6-dimethyl-4-pyridinyl)-9-fluoro-3-methyl-7-oxo-2,3-dihydro-7H-pyrido[1,2,3-de][1,4]benzothiazine-6-carboxylate and 10 ml of 1M hydrochloric acid was heated at reflux for two hours. The reaction mixture was poured into ice-water and extracted with chloroform. The extract was dried (sodium sulfate), filtered and concentrated to give 0.84 g of solid product which was recrystallized from acetonitrile to yield 0.62 g of (S)-10-(2,6-dimethyl-4-pyridinyl)-9-fluoro-3-methyl-7-oxo-2,3-dihydro-7H-pyrido[1,2,3-de][1,4]benzothiazine-6-carboxylic acid, colorless crystalline powder, m.p. 328°–331° C.; $[\alpha]_D^{25} = +56.3°$.

EXAMPLE 8

(a) Ethyl (S)-(4-bromo-2,3,4-trifluorobenzoyl)-N-(1-hydroxy-2-butyl)-3-aminopropenoate

[XII; Alk and R''=C$_2$H$_5$] was prepared from 4-bromo-2,3,5-trifluorobenzoylacetate (Example 6b), dimethylformamide and (S)-2-amino-1-butanol by the procedure of Example 1(d), and was obtained in the form of an oil used directly in the next reaction.

(b) Ethyl (S)-7-bromo-6,8-difluoro-1-(1-hydroxy-2-butyl)-1,4-dihydro-4-oxo-3-quinolinecarboxylate

[XIII; Alk and R"=C$_2$H$_5$] was prepared from the crude product of part (a) and lithium carbonate according to the procedure of Example 7(b), and was obtained in 62% yield as a solid, m.p. 200°–201° C. when recrystallized from acetonitrile..

(c) Ethyl (S)-7-(2,6-diemthyl-4-pyridinyl)-6,8-difluoro-1-(1-hydroxy-2-butyl)-1,4-dihydro-4-oxo-3-quinolinecarboxylate

[XIV; Alk and R"=C$_2$H$_5$] was prepared from the product of part (b) and 2,6-dimethyl-4-(trimethylstannyl)pyridine in the presence of palladium catalyst according to the procedure of Example 2, and was obtained in about 60% yield as a colorless solid, m.p. 183°–186° C.

(d) (S)-10-(2,6-Dimethyl-4-pyridinyl)-9-fluoro-3-ethyl-7-oxo-2,3-dihydro-7H-pyrido[1,2,3-de][1,4]genzoxazine-6-carboxylic acid

[I; R and R'=H, R"=C$_2$H$_5$] was prepared by cyclization of the product of part (c) with potassium carbonate heated together in dimethylformamide solution, and hydrolyzing the resulting ester with hydrochloric acid. The product was obtained in about 30% yield in the form of colorless plates, m.p. 239°–240° C. when recrystallized from methanol; $[\alpha]_D^{25} = -70.1°$ (1% in chloroform.

The in vitro antimicrobial activity of the compounds of the invention was determined by a microplate dilution procedure. Bacterial cultures were grown in Meuller Hintom II (cation supplemented) broth (*S. aureus, S. faecalis, M. luteus, E. coli* and *P. aeruginosa*), Brain Heart Infusion (BHI) broth supplemented with 10% heat inactivated horse serum (*S. penumoniae*) or BHI broth supplemented with 5 mcg/ml Hemin and 0.5 mcg/ml vitamin K (*B. fragilis*) at 37° C. for 18–24 hrs. The cultures were grown under aerobic conditions with the exception of *B. fragilis* which was grown 48 hrs. under anaerobic conditions (atmosphere 5% CO$_2$, 10% H$_2$ and 85% N$_2$). Resulting suspensions were diluted 1/10 in the appropriate broth or used undiluted for the inoculum. Aqueous solutions of the compounds of the invention were solubilized in dimethylsulfoxide (DMSO) at the desired concentration and 200 mcl were dispensed into the first row of wells of a sterile microplate. The compounds were then serially diluted twofold in DMSO to give a working stock concentration range plate. The last row of wells was left compound-free receiving only DMSO to serve as a growth control. Five mcl from each well of the working stock plate was transferred to corresponding wells of a separate plate containing 95 mcl/well of the appropriate broth. All dilutions were made with either an automated dilutor or manually. The wells of microplate containing the desired compound concentrations and compound-free growth controls in broth were then inoculated using the MIC 2000 inoculator which delivers 1.5 mcl/well to give a final inoculum level of 10$^4$ microorganism/well or 10$^5$ microorganism/ml. Plates were incubated as described above and read for visible growth. The minimal inhibitory concentration (MIC: expressed in mcg/ml) of each compound tested against each test microorganism was determined as the lowest concentration of compound which prevents visible microbial growth.

The following compounds were tested according to the foregoing procedure:

A. (S)-10-(2,6-Dimethyl-4-pyridinyl)-8,9-difluoro-3-methyl-7-oxo-2,3-dihydro-7H-pyrido[1,2,3-de][1,4]benzoxazine-6-carboxylic acid (Examples 1h and 2b).

B. (S)-10-(2,6-Dimethyl-4-pyridinyl)-9-fluoro-3-methyl-7-oxo-2,3-dihydro-7H-pyrido[1,2,3-de][1,4]benzoxazine-6-carboxylic acid (Example 3c).

C. (S)-10-(2,6-Dimethyl-4-pyridinyl)-9-fluoro-3-ethyl-7-oxo-2,3-dihydro-7H-pyrido[1,2,3-de][1,4]benzoxazine-6-carboxylic acid (Example 8d).

D. (S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid (Example 7f.)

Prior art compounds:

P. 9-Fluoro-3-methyl-10-(4-methyl-1-piperazinyl)-7-oxo-2,3-dihydro-7H-pyrido[1,2,3-de][1,4]benzoxazine-6-carboxylic acid.

Q. 7-(2,6-Dimethyl-4-pyridinyl)-1-ethyl-6-fluoro-1,4-dihydro-4-oxo-3-quinolinecarboxylic acid.

The following Table I summarizes the results of the testing of the foregoing compounds:

TABLE I

| Com-pound | In vitro (mcg/ml) | | | | | | |
|---|---|---|---|---|---|---|---|
| | ML MIC | EC MIC | SA MIC | SF MIC | SP MIC | PA MIC | BF MIC |
| A | 1 | 0.125 | 0.016 | 0.125 | 0.06 | 8 | 1 |
| B | 0.25 | 0.03 | 0.008 | 0.06 | 0.03 | 4 | 0.25 |
| C | 0.5 | 0.016 | <0.004 | 0.125 | 0.06 | 4 | 0.5 |
| D | 0.06 | 0.06 | 0.004 | 0.06 | 0.016 | 2 | 0.06 |
| P | 2 | 0.008 | 0.25 | 2 | 0.25 | 0.5 | 0.5 |
| Q | 0.5 | 0.06 | 0.03 | 0.25 | 0.25 | 4 | 2 |

ML = *Micrococcus luteus*
EC = *Escherichia coli*
SA = *Staphylococcus aureus*
SF = *Streptococcus faecalis*
SP = *Streptococcus pneumoniae*
PA = *Pseudomonas aeruginosa*
BF = *Bacteroides fragilis*

It will be seen from the above Table that compounds B and D are substantilly more active than the prior art compounds (P and Q) against all of the organisms except *E. coli* and *P. aeruginosa*; and compounds A and C show improved activity against *Staph. auerus, Strep. faecalis* and *Strip. pneumoniae*. The improvement in activity is particularly marked in the case of the important pathogen *Staph. aureus*, where compound B is thirty times as active as compound P and four times as active as compound Q; and compound D is sixty times as active as compound P and eight times as active as compound Q.

The in vivo antibacterial activity of the compounds of the invention was determined in female mice, 18–20 grams each. Aqueous solutions of the compounds to be tested were prepared by dissolving the free acid form in dilute sodium hydroxide and diluting the solution with distilled water to the desired concentration.

Cultures of *E. coli* were grown in brain heart infusion broth, and the mice were inoculated intraperitoneally with 0.5 ml of the bacterial test inoculum suspended in saline. Cultures of *Staph. aureus* were thawed from frozen pooled stocks and mixed with 5% mucin. A 0.5 ml preparation was used to infect mice by i.p. inoculation.

The mice were medicated subcutaneously (sc) or orally (po) with 0.5 ml of the test compound solution one-half hour postinfection. Deaths were recorded daily for seven days. Fifty percent protective dose values (PD$_{50}$) were calculated using probit analyis. The results are given in the following Table II.

TABLE II

| | In vivo (Mouse, mg/kg) | | | |
|---|---|---|---|---|
| | Staph. aureus | (PD$_{50}$) | E. coli | (PD$_{50}$) |
| Compound | sc | po | sc | po |
| A | 0.05 | 0.13 | 4.7 | 12.3 |
| B | 0.02 | 0.03 | 1.4 | 3.0 |
| C | 0.2 | 0.41 | 8.8 | 32.9 |
| D | 0.03 | 0.03 | 1.5 | 2.6 |
| P | 3.0 | 6.5 | 0.48 | 1.17 |
| Q | 0.71 | 1.38 | 5.39 | 8.24 |

It will be seen from the above Table II that, although the compounds A, B and D are approximately equal in activity to compound Q and slightly less active than compound P against *E. coli*, the new compounds are markedly more active (15-200 times) than the prior art compounds against *Staph. aureus*. Compound C is fifteen and three times more active than compounds P and Q, respectively, against *Staph. aureus* by subcutaneous administration.

In monkeys, compound B gave high and prolonged serum levels after 25 mg/kg oral dosing: maximum concentration of 25 μg/ml at 3.5 hours with a half-life of 16 hours.

The compound of Example 4, (S)-8-(benzylthio)-10-(2,6-dimethyl-4-pyridinyl)-9-fluoro-3-methyl-7-oxo-2,3-dihydro-7H-pyrido[1,2,3-de][1,4]benzoxazine-6-carboxylic acid, also was found to have appreciable antibacterial activity in vitro, MIC (μg/ml) values as follows: *M. luteus* (32), *E. coli* (8), *Staph. aureus* (1), *Strep. faecalis* (32), *Strep. pneumoniae* (8) and *B. fragilis* (32).

The compound of Example 6(e), ethyl (R)-10-(2,6-dimethyl-4-pyridinyl)-9-fluoro-3-methyl-7-oxo-2,3-dihydro-7H-pyrido[1,2,3-de][1,4]benzoxazine-6-carboxylate, while less active than the (S)-isomer (compound B), was found to have substantial antibacterial activity in vitro, MIC (μg/ml) values as follows: *E. coli* (1.0), *Staph. aureus* (0.25), *Strep. faecalis* (4), *Strep. pneumoniae* (1) and *B. fragilis* (16).

The compounds of the invention can be prepared for use by conventional pharmaceutical procedures: that is, by dissolving or suspending them in a pharmaceutically acceptable vehicle, e.g., water, aqueous alcohol glycol, oil solution or oil-water emulsion, for parenteral or oral administration or topical application; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

I claim:

1. A compound having the formula:

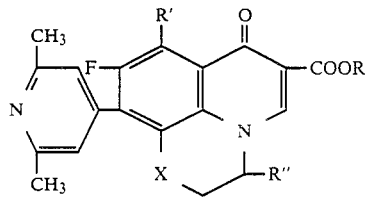

wherein:
R is hydrogen or lower-alkyl;
R' is selected from the group consisting of hydrogen, fluoro and —SR''', where R''' is benzyl, phenyl or lower-alkyl;
R'' is alkyl of 1-3 carbon atoms;
X is O or S; a pharmaceutically acceptable acid-addition salt thereof; or an alkali metal or amine salt of a compound where R is hydrogen.

2. A compound according to claim 1 wherein R is hydrogen and R' is hydrogen or fluoro.

3. (S)-10-(2,6-Dimethyl-4-pyridinyl)-8,9-difluoro-3-methyl-7-oxo-2,3-dihydro-7H-pyrido[1,2,3-de]-[1,4]benzoxazine-6-carboxylic acid, according to claim 2.

4. (S)-10-(2,6-Dimethyl-4-pyridinyl)-9-fluoro-3-methyl-7-oxo-2,3-dihydro-7H-pyrido[1,2,3-de][1,4]benzoxazine-6-carboxylic acid, according to claim 2.

5. (S)-10-(2,6-Dimethyl-4-pyridinyl)-9-fluoro-3-ethyl-7-oxo-2,3-dihydro-7H-pyrido[1,2,3-de][1,4]benzoxazine-carboxylic acid, according to claim 2.

6. (S)-10-(2,6-Dimethyl-4-pyridinyl)-9-fluoro-3-methyl-7-oxo-8-(benzylthio)-2,3-dihydro-7H-pyrido[1,2,3-de][1,4]benzoxazine-6-carboxylic acid, according to claim 1.

7. (S)-10-(2,6-Dimethyl-4-pyridinyl)-9-fluoro-3-methyl-7-oxo-2,3-dihydro-7H-pyrido[1,2,3-de][1,4]benzothiazine-6-carboxylic acid, according to claim 2.

8. A composition for combating bacteria, which comprises an antibacterially effective amount of a compound according to claim 2 together with one or more pharmaceutically acceptable excipients or diluents.

9. A method for combating bacteria, which comprises contacting the locus of said bacteria with a composition according to claim 8.

10. A method for combating a bacterial infection in a mammalian host which comprises administering to said host an antibacterially effective amount of a composition according to claim 8.

* * * * *